United States Patent
Reggiani et al.

(10) Patent No.: US 9,162,022 B2
(45) Date of Patent: *Oct. 20, 2015

(54) OXYGENATOR WITH INTEGRATED ARTERIAL FILTER INCLUDING FILTER FRAME

(71) Applicants: Sorin Group Italia S.r.l., Milan (IT); Politecnico di Milano, Milan (IT)

(72) Inventors: Stefano Reggiani, Medolla (IT); Claudio Silvestri, Quarantoli Mirandola (IT); Alberto Giri, Mirandola (IT); Alberto Redaelli, Milan (IT); Gianfranco Beniamino Fiore, Milan (IT)

(73) Assignees: Politecnico di Milano, Milan (IT); Sorin Group Italia S.r.l., Milan (IT)

( * ) Notice: Subject to any disclaimer, the term of this patent is extended or adjusted under 35 U.S.C. 154(b) by 307 days.

This patent is subject to a terminal disclaimer.

(21) Appl. No.: 13/750,531

(22) Filed: Jan. 25, 2013

(65) Prior Publication Data

US 2013/0142695 A1 Jun. 6, 2013

Related U.S. Application Data

(63) Continuation of application No. 12/899,283, filed on Oct. 6, 2010, now Pat. No. 8,388,566, which is a continuation-in-part of application No. 12/770,327, filed on Apr. 29, 2010, now Pat. No. 8,318,092.

(30) Foreign Application Priority Data

Oct. 5, 2010 (EP) .................................. 10186550

(51) Int. Cl.
*A61M 37/00* (2006.01)
*A61M 1/16* (2006.01)
(Continued)

(52) U.S. Cl.
CPC ............ *A61M 1/1698* (2013.01); *A61M 1/322* (2014.02); *A61M 1/3627* (2013.01)

(58) Field of Classification Search
USPC .................... 604/4.01, 5.01, 6.01, 6.14, 6.09; 422/44, 48
See application file for complete search history.

(56) References Cited

U.S. PATENT DOCUMENTS 3,957,648 A 5/1976 Roget et al.
4,038,190 A 7/1977 Baudet et al.
(Continued)

FOREIGN PATENT DOCUMENTS

EP 0312125 A1 4/1989
EP 0582959 A1 2/1994
(Continued)

OTHER PUBLICATIONS

European Search Report issued in EP Application No. 10161451, dated Sep. 28, 2010, 5 pages.
(Continued)

*Primary Examiner* — Leslie Deak
(74) *Attorney, Agent, or Firm* — Faegre Baker Daniels LLP

(57) ABSTRACT

An oxygenator combines, in a single structure, a heat exchanger, a gas exchanger, an arterial filter, and a filter frame. Such an oxygenator permits fewer fluid connections and thus may simplify an extracorporeal blood circuit, including a heart-lung machine and a blood reservoir, in which it is used. In some embodiments, the oxygenator may be configured to include multiple purge ports for purging bubbles both before and after filtering the blood.

12 Claims, 13 Drawing Sheets

(51) Int. Cl.
*A61M 1/36* (2006.01)
*A61M 1/32* (2006.01)

(56) References Cited

U.S. PATENT DOCUMENTS

| | | | |
|---|---|---|---|
| 4,229,305 | A | 10/1980 | Fecondini et al. |
| 4,597,868 | A | 7/1986 | Watanabe |
| 4,639,353 | A | 1/1987 | Takemure et al. |
| 4,902,476 | A | 2/1990 | Gordon et al. |
| 5,169,530 | A | 12/1992 | Schucker et al. |
| 5,192,439 | A | 3/1993 | Roth et al. |
| 5,192,499 | A | 3/1993 | Sakai et al. |
| 5,270,004 | A | 12/1993 | Cosentino et al. |
| 5,316,724 | A | 5/1994 | Mathewson et al. |
| 5,338,512 | A | 8/1994 | Mathewson et al. |
| 5,514,095 | A | 5/1996 | Brightbill et al. |
| 5,578,267 | A | 11/1996 | Cosentino et al. |
| 5,674,452 | A | 10/1997 | Carson et al. |
| 5,733,398 | A | 3/1998 | Carson et al. |
| 5,762,868 | A | 6/1998 | Leonard |
| 5,762,869 | A | 6/1998 | White et al. |
| 5,817,278 | A | 10/1998 | Fini et al. |
| 5,817,279 | A | 10/1998 | Eilers et al. |
| 5,830,370 | A | 11/1998 | Maloney, Jr. et al. |
| RE36,774 | E | 7/2000 | Cosentino et al. |
| 6,105,664 | A | 8/2000 | Gillbrand et al. |
| 6,113,782 | A | 9/2000 | Leonard |
| 6,241,945 | B1 | 6/2001 | Owen |
| 6,454,999 | B1 | 9/2002 | Farhangnia et al. |
| 6,755,894 | B2 | 6/2004 | Bikson et al. |
| 6,960,322 | B2 | 11/2005 | Stringer et al. |
| 8,318,092 | B2 | 11/2012 | Reggiani et al. |
| 8,388,566 | B2 | 3/2013 | Reggiani et al. |
| 8,394,049 | B2 | 3/2013 | Reggiani et al. |
| 8,652,406 | B2 | 2/2014 | Reggiani et al. |
| 8,795,220 | B2 | 8/2014 | Reggiani et al. |
| 2002/0039543 | A1 | 4/2002 | Ikeda et al. |
| 2003/0080047 | A1 | 5/2003 | Watkins et al. |
| 2004/0175292 | A1 | 9/2004 | Ghellil et al. |
| 2004/0251011 | A1 | 12/2004 | Kudo |
| 2007/0107884 | A1 | 5/2007 | Sirkar et al. |
| 2007/0166190 | A1 | 7/2007 | Ogihara et al. |
| 2007/0231203 | A1 | 10/2007 | Mizoguchi et al. |
| 2008/0234623 | A1 | 9/2008 | Strauss et al. |
| 2010/0269342 | A1 | 10/2010 | Carpenter et al. |
| 2010/0272606 | A1 | 10/2010 | Carpenter et al. |
| 2010/0272607 | A1 | 10/2010 | Carpenter et al. |
| 2011/0268608 | A1 | 11/2011 | Reggiani et al. |
| 2011/0268609 | A1 | 11/2011 | Reggiani et al. |
| 2012/0046594 | A1 | 2/2012 | Reggiani et al. |
| 2012/0121463 | A1 | 5/2012 | Reggiani et al. |
| 2012/0294761 | A1 | 11/2012 | Reggiani et al. |
| 2013/0142696 | A1 | 6/2013 | Reggiani et al. |
| 2014/0227133 | A1 | 8/2014 | Reggiani et al. |

FOREIGN PATENT DOCUMENTS

| | | |
|---|---|---|
| EP | 0895786 A1 | 2/1999 |
| EP | 1108462 A2 | 6/2001 |
| EP | 1180374 A1 | 2/2002 |
| EP | 1371381 A1 | 12/2003 |
| EP | 1834656 B1 | 9/2007 |
| JP | 2007190218 A | 2/2007 |
| WO | WO9716213 A2 | 5/1997 |
| WO | WO9719714 A1 | 6/1997 |
| WO | WO9733636 A1 | 9/1997 |
| WO | WO2010124087 A1 | 10/2010 |

OTHER PUBLICATIONS

European Search Report issued in EP Application No. 10173436, dated Feb. 14, 2011, 7 pages.

European Search Report issued in EP Application No. 10186550, dated Jan. 27, 2011, 7 pages.

International Search Report and Written Opinion issued in PCT/IB2012/052424, mailed Oct. 24, 2012, 17 pages.

International Search Report issued in PCT/IB2011/054725, mailed Feb. 9, 2012, 12 pages.

European Search Report issued in EP Application No. 10191140, mailed Nov. 30, 2011, 8 pages.

European Search Report issued in EP Application No. 12187501, mailed Nov. 20, 2013, 6 pages.

European Search Report issued in EP Application No. 13161841, mailed Jun. 11, 2013, 6 pages.

OXYGENATOR WITH INTEGRATED ARTERIAL FILTER INCLUDING FILTER FRAME

RELATED APPLICATIONS

This application is a continuation of U.S. application Ser. No. 12/899,283, filed Oct. 6, 2010, which is a continuation-in-part of U.S. application Ser. No. 12/770,327, filed Apr. 29, 2010, and which claims priority to European Application No. 10186550.9, filed Oct. 5, 2010.

TECHNICAL FIELD

The disclosure pertains generally to arterial filters used in blood perfusion systems.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral, or other artery.

Often, an arterial filter is added to the extracorporeal circuit, after the oxygenator, as last barrier before the patient, so as to block any solid or gaseous emboli and prevent any such emboli from entering into the aorta of the patient. Recently, arterial filters integrated in the oxygenator have been developed, allowing the reduction of the priming volume of the circuit and decreasing the global haemodilution of the patient.

SUMMARY

Example 1 is a blood processing apparatus that includes an apparatus housing having a blood inlet and a blood outlet, the blood inlet extends into an interior of the apparatus housing. A heat exchanger is disposed about the blood inlet and in fluid communication therewith. A gas exchanger is disposed about the heat exchanger and in fluid communication therewith. A filter housing is coupled about the apparatus housing and defining a filter volume between the apparatus housing and the filter housing, the filter volume is in fluid communication with the gas exchanger via one or more openings that are formed within the apparatus housing such that blood exiting the gas exchanger can pass into the filter volume. A filter assembly is disposed within the filter housing. The filter assembly includes a filter frame having one or more ribs and a filter net disposed on the filter frame. The one or more ribs align with at least a portion of the one or more openings so as to reduce blood velocity through at least a portion of the filter net.

In Example 2, the blood processing apparatus of Example 1 in which one or more openings comprise a plurality of openings arranged along an arcuate path. The one or more ribs comprise arcuate ribs aligned with the arcuate path.

In Example 3, the blood processing apparatus of Example 1 in which the filter frame has a first annular frame ring having a first diameter, a second annular frame ring having a second diameter, greater than the first diameter, and one or more bridge elements extending between the first annular frame ring and the second annular frame ring.

In Example 4, the blood processing apparatus of Example 3 in which one or more ribs are disposed between the first annular frame ring and the second annular frame ring.

In Example 5, the blood processing apparatus of Example 1 in which the filter frame includes a plate portion arranged near the blood outlet to limit preferential blood flow through the filter assembly near the blood outlet.

In Example 6, the blood processing apparatus of Example 1 in which the filter assembly divides the filter volume into a first chamber between the filter assembly and the apparatus housing and a second chamber between the filter assembly and the filter housing.

In Example 7, the blood processing apparatus of Example 6, in which further comprises a first purge port in fluid communication with the first chamber and a second purge port in fluid communication with the second chamber.

In Example 8, the blood processing apparatus of Example 7 in which the filter housing has a frustoconical configuration having a smaller diameter at one end and a larger diameter at an opposing end. The second purge port is located near the larger diameter end of the filter housing.

In Example 9, the blood processing apparatus of Example 8 in which the first purge port is located near the smaller diameter end of the filter housing.

In Example 10, the blood processing apparatus of Example 7 in which bubbles within the blood can exit through the first purge port and/or the second purge port.

In Example 11, the blood processing apparatus of Example 1 in which the gas exchanger is configured to permit gas to flow therethrough in order to add oxygen and remove carbon dioxide from the blood passing through the gas exchanger.

In Example 12, the blood processing apparatus of Example 1 in which the filter assembly includes a biocompatible coating on the filter net.

In Example 13, the blood processing apparatus of Example 1 in which the filter net comprises a polyester filter net or a polypropylene filter net.

Example 14 is a blood processing apparatus that includes an apparatus housing having a blood inlet and a blood outlet, the blood inlet extending into an interior of the apparatus housing. A heat exchanger core extends coaxially within the apparatus housing and is axially aligned with the blood inlet. Heat exchanger hollow fibers are disposed about the heat exchanger core such that a heat exchanger fluid may flow through the heat exchanger hollow fibers and blood passing from the blood inlet may flow across the heat exchanger hollow fibers. A cylindrical shell extends coaxially about the heat exchanger core. The cylindrical shell includes an annular shell aperture that is disposed near an end of the cylindrical shell opposite to an end near the blood inlet. The annular shell aperture is configured to permit blood to pass to an exterior of the cylindrical shell. Gas exchanger hollow fibers are disposed about the cylindrical shell such that gases may flow through the gas exchanger hollow fibers and blood passing from the annular shell aperture may flow across the gas exchanger hollow fibers. A filter housing is coupled about the apparatus housing and defines a filter volume between the apparatus housing and the filter housing. The filter volume is in fluid communication with the gas exchanger via one or more openings that are formed within the apparatus housing along an arcuate path such that blood exiting the gas exchanger can pass into the filter volume. A filter assembly is disposed within the filter housing and divides the filter volume into a first chamber between the filter assembly and the apparatus housing and a second chamber between the filter assembly and the filter housing. The filter assembly includes a filter frame with one or more arcuate ribs and a filter net disposed on the filter frame. The one or more arcuate ribs are aligned with the one or more openings along the arcuate path in order to slow blood velocity through the filter net. The blood processing apparatus includes a first purge port that is in fluid communication with the first chamber and a second purge port that is in fluid communication with the second chamber.

In Example 15, the blood processing apparatus of Example 14 in which the filter assembly includes a biocompatible coating on the filter net.

In Example 16, the blood processing apparatus of Example 14 in which the filter net comprises a polyester filter net or a polypropylene filter net.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a blood processing apparatus that combines, in a single structure, a heat exchanger, a gas exchanger or oxygenator and an arterial filter. In some embodiments, the term oxygenator may be used to refer to a structure that combines a heat exchanger, a gas exchanger and an arterial filter in a unitary device. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator. In some embodiments, by incorporating the arterial filter with the oxygenator, the tubing set used to create the extracorporeal blood circuit may be reduced in complexity or number of parts and thus may simplify the extracorporeal blood circuit. In some embodiments, this will reduce the priming volume of the extracorporeal blood circuit.

Figure 1:
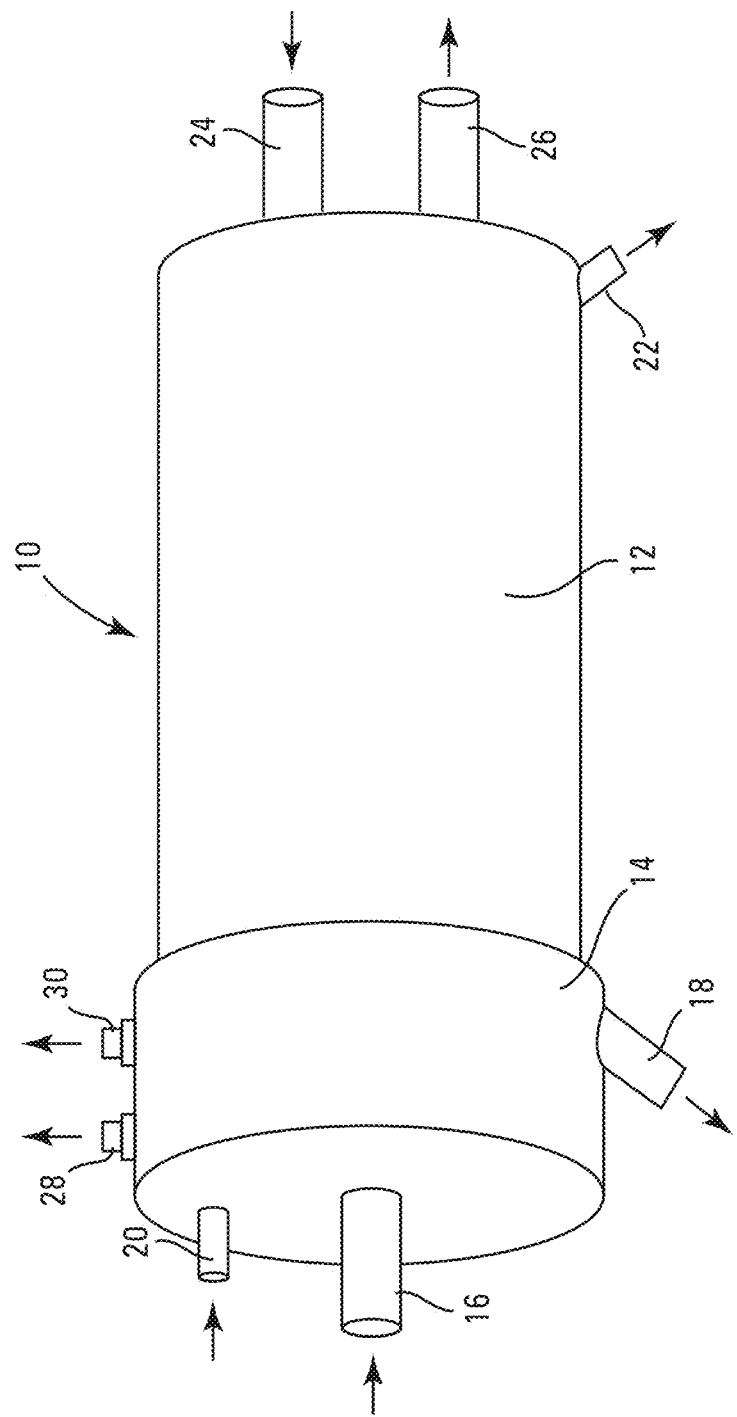
FIG. 1 is a schematic illustration of a blood processing apparatus including an integrated arterial filter in accordance with an embodiment of the invention.

FIG. 1 is a schematic illustration of a blood processing apparatus or oxygenator 10. While the internal components are not visible in this illustration, the oxygenator 10 may include one or more of a heat exchanger, a gas exchanger and an arterial filter. According to some embodiments, each of the heat exchanger, gas exchanger and arterial filter are integrated into a single structure that forms an oxygenator housing. The oxygenator 10 includes a device compartment or housing 12 and an arterial filter compartment or housing 14. In some embodiments, the arterial filter housing 14 may be integrally molded or otherwise structurally integrated with the device housing 12. In some cases, the arterial filter housing 14 may be separately formed and then secured or otherwise coupled to the device housing 12. According to various embodiments, the heat exchanger, the gas exchanger, and the arterial filter housing 14 may have a cross-section shaped generally as a circle or as a parallelogram (e.g., a square or rectangle). Each of the heat exchanger, the gas exchanger and the arterial filter housing 14 may have generally the same sectional shape or each may have a different sectional shape.

In some embodiments, a blood inlet 16 extends through the arterial filter housing 14 and into the device housing 12. A blood outlet 18 exits the arterial filter housing 14. As noted, in some embodiments the oxygenator 10 includes a gas exchanger and thus may include a gas inlet 20 and a gas outlet 22. In some embodiments, the oxygenator 10 includes a heat exchanger and thus may include a heating fluid inlet 24 and a heating fluid outlet 26. As will be explained in greater detail with respect to FIG. 2, the oxygenator 10 includes a first purge port 28 and a second purge port 30. The positions of the inlets, outlets and purge ports are merely illustrative, as other arrangements and configurations are contemplated. The purge ports may include a valve or a threaded cap. The purge ports operate to permit gases (e.g., air bubbles) that exit the blood to be vented or aspirated and removed from the oxygenator.

Figure 2:
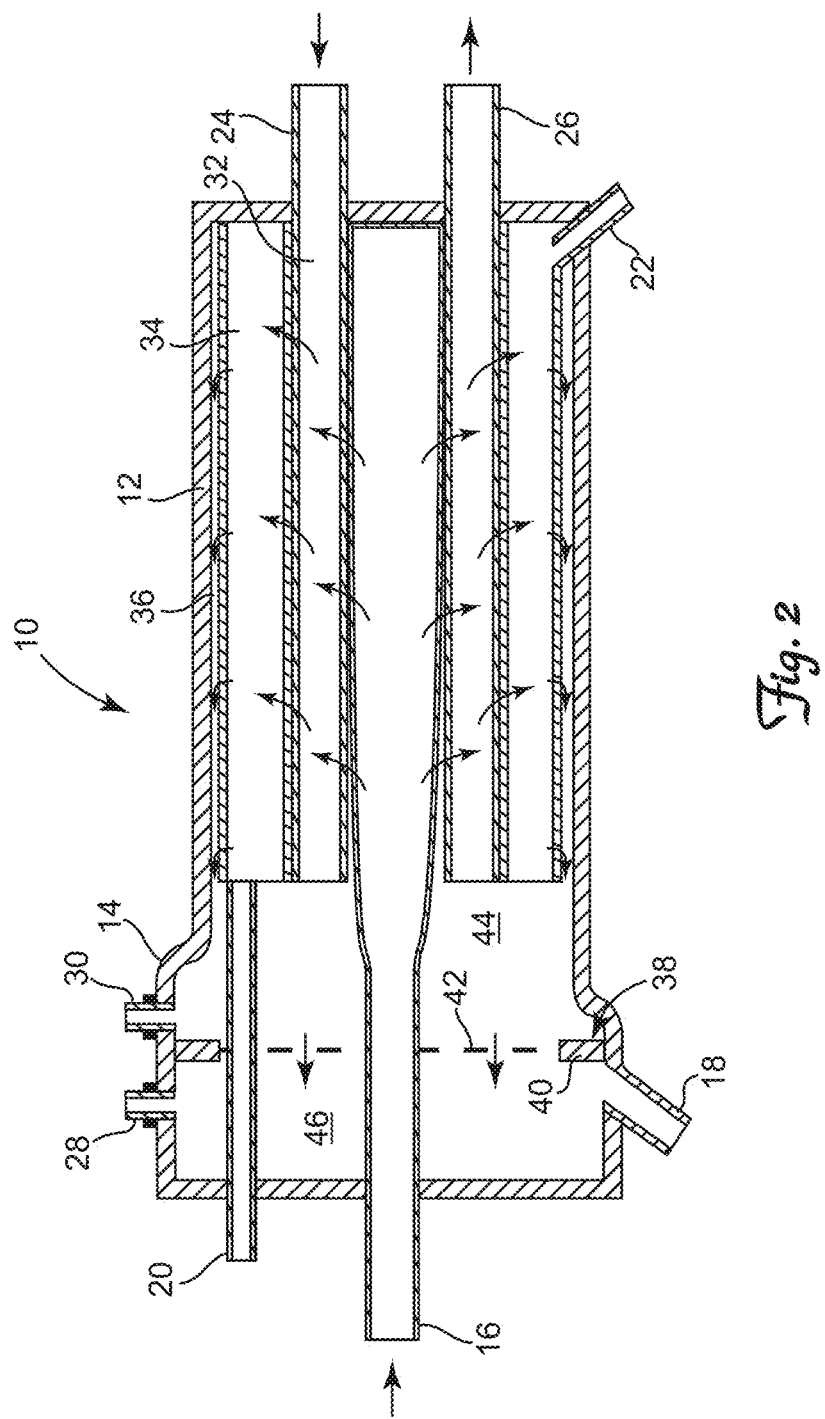
FIG. 2 is a cross-sectional illustration of the blood processing apparatus of FIG. 1.

FIG. 2 is a cross-sectional view of the oxygenator 10, illustrating internal components and exemplary blood flow through the oxygenator 10. The oxygenator 10 includes a heat exchanger 32 and a gas exchanger 34. In some embodiments, the heat exchanger 32 includes a number of hollow fibers through which a heating fluid such as water can flow. The blood may flow around and past the hollow fibers and thus be suitably heated. In some embodiments, the hollow fibers may be polymeric. In some cases, metallic fibers may be used within the heat exchanger 32. According to other embodiments, the heat exchanger 32 includes a metal bellows or other structure comprising a substantial surface area (e.g., fins) for facilitating heat transfer with the blood.

In some embodiments the gas exchanger 34 may include a number of microporous hollow fibers through which a gas such as oxygen may flow. The blood may flow around and past the hollow fibers. Due to concentration gradients, oxygen may diffuse through the hollow fibers into the blood while carbon dioxide may diffuse into the hollow fibers and out of the blood.

The oxygenator 10, according to some embodiments, includes an annular space 36 into which blood may flow as the blood exits the gas exchanger 34. As illustrated, the annular space 36 may extend into the arterial filter housing 14. According to exemplary embodiments, the annular space 36 may be generally circular or generally rectangular. The arterial filter housing 14 includes a filter 38. In some embodiments, the filter 38 includes an annular frame 40 and a net or mesh 42 spanning the annular frame 40. In some embodiments, the filter 38 may be considered as dividing a volume within the arterial filter housing 14 into a first chamber 44 and a second chamber 46. In various embodiments, the annular frame 40 and the net or mesh 42 are disposed concentrically with respect to the filter housing 14. In other embodiments the annular frame 40 and the mesh 42 are disposed about the housing 14 in a non-concentric manner. According to exemplary embodiments, the internal (i.e., priming) volume of the arterial filter housing 14 is between about 30 to about 150 mL or from about 80 and about 110 mL. According to other embodiments, the priming volume is between about 30 to 150 mL or from about 90 and about 100 mL.

In some embodiments, the annular space 36 may open into or otherwise be in fluid communication with the first chamber 44. While blood is in the first chamber 44, any air bubbles that are present within the blood may be vented through the second purge port 30. Blood may pass through the filter 38 and into the second chamber 46. Any bubbles remaining in the blood, or caused by passage through the filter 38, may be vented through the first purge port 28. Blood may then exit the oxygenator 10 through the blood outlet 18. The presence of the first purge port 28 in the second chamber 46 and the second purge port 30 in the first chamber 44, according to various embodiments, will improve the priming speed due to the fact that bubbles present in the blood have both a first and a second opportunity to exit through a purge port. Moreover, in these embodiments, the efficacy of the bubble or gas removal is improved, again due to the fact that bubbles present in the blood have both a first and a second opportunity to exit through a purge port.

Figure 3:
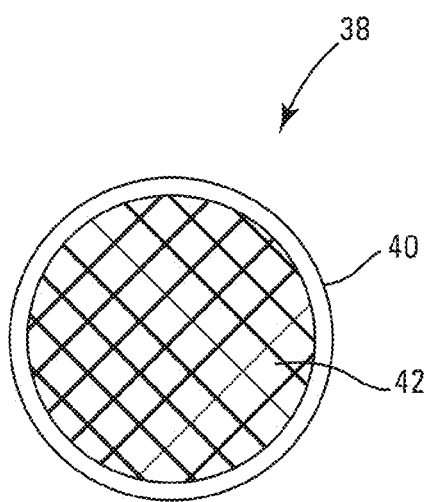
FIG. 3 is an illustrative view of a filter deployed within the blood processing apparatus of FIG. 1.
Figure 4:
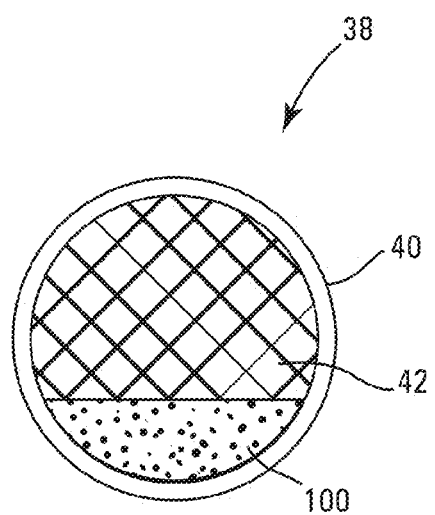
FIG. 4 is an illustrative view of another filter deployed within the blood processing apparatus of FIG. 1.

FIG. 3 is a view of the filter 38, illustrating the frame 40 and the net or mesh 42. FIG. 4 shows an embodiment of the filter 38 including a blocking plate 100. In some embodiments, the blocking plate 100 may be sized, shaped and positioned near the blood outlet 18 to limit preferential blood flow on the lower portion of the oxygenator 10. According to various embodiments, the filter 38 may have a cross-sectional shape that is circular, rectangular, or any other shape.

In some embodiments, the net or mesh 42 may have a mesh size that is the range of about 20 to about 200 microns. In some cases, the net or mesh 42 may have a mesh size of about 120 microns. In some instances, the net or mesh 42 may have a mesh size of from about 38-40 microns, and may be formed of a polymeric material such as polyester or polypropylene. In some cases, the net 42 may be coated with a biocompatible material. The blocking plate 100 may be formed of any suitable material. In some embodiments, the blocking plate 100 may be integrally formed with the frame 40. According to various exemplary embodiments, the net or mesh 42 has a surface area of between about 70 and about 90 square centimeters. According to other exemplary embodiments, the net or mesh 42 has a surface are of between about 75 and about 80 square centimeters.

Figure 5:
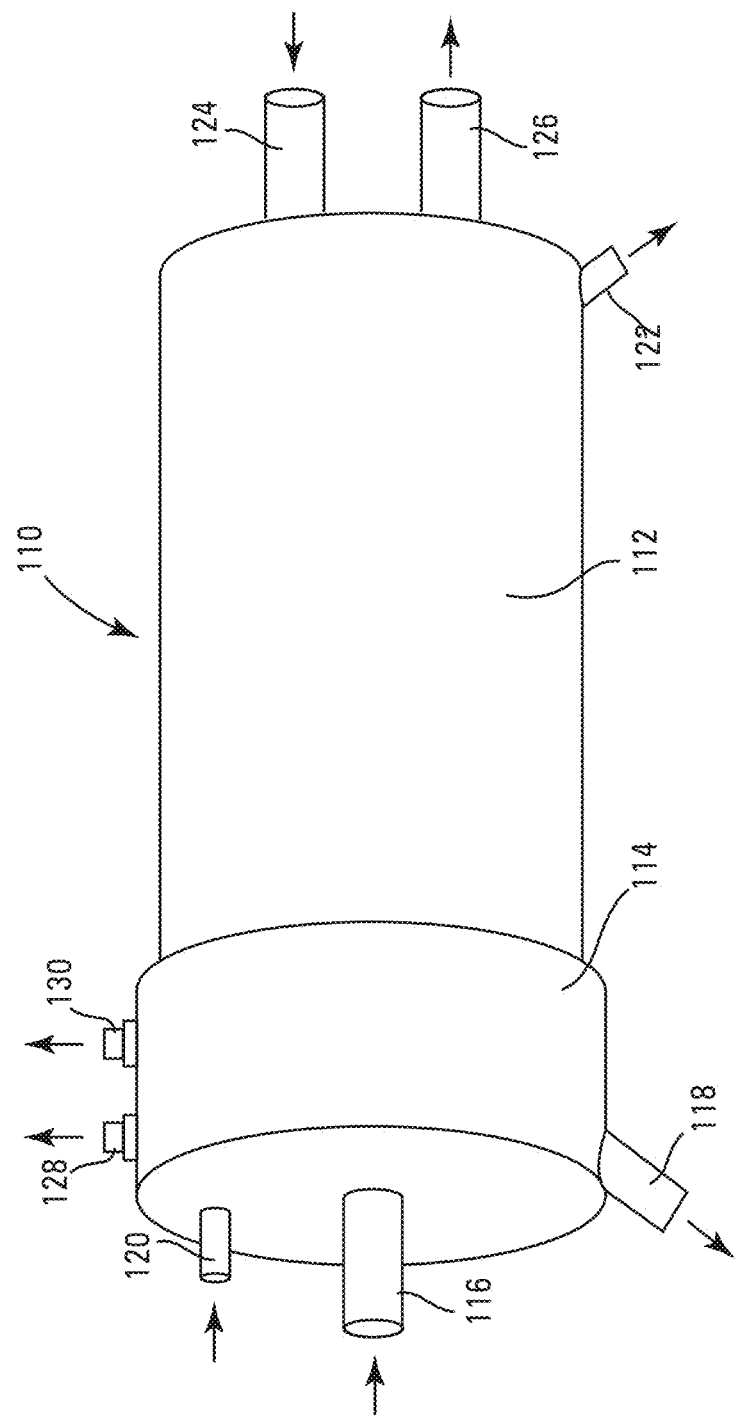
FIG. 5 is a schematic illustration of a blood processing apparatus including an integrated arterial filter in accordance with an embodiment of the invention.

FIG. 5 is a schematic illustration of a blood processing apparatus or oxygenator 110. While the internal components are not visible in this illustration, the oxygenator 110 may include one or more of a heat exchanger, a gas exchanger and an arterial filter. The oxygenator 110 includes a device housing 112 and an arterial filter housing 114. In some embodiments, the arterial filter housing 114 may be integrally molded or otherwise formed with the device housing 112. In some cases, the arterial filter housing 114 may be separately formed and then secured to the device housing 112.

In some embodiments, a blood inlet 116 extends through the arterial filter housing 114 and into the device housing 112. A blood outlet 118 exits the arterial filter housing 114. As noted, in some embodiments the oxygenator 110 includes a gas exchanger and thus may include a gas inlet 120 and a gas outlet 122. In some embodiments, the oxygenator 110 includes a heat exchanger and thus may include a heating fluid inlet 124 and a heating fluid outlet 126. As will be explained in greater detail with respect to FIG. 6, the oxygenator 110 includes a first purge port 128 and a second purge port 130. The positions of the inlets, outlets and purge ports are merely illustrative, as other arrangements and configurations are contemplated.

Figure 6:
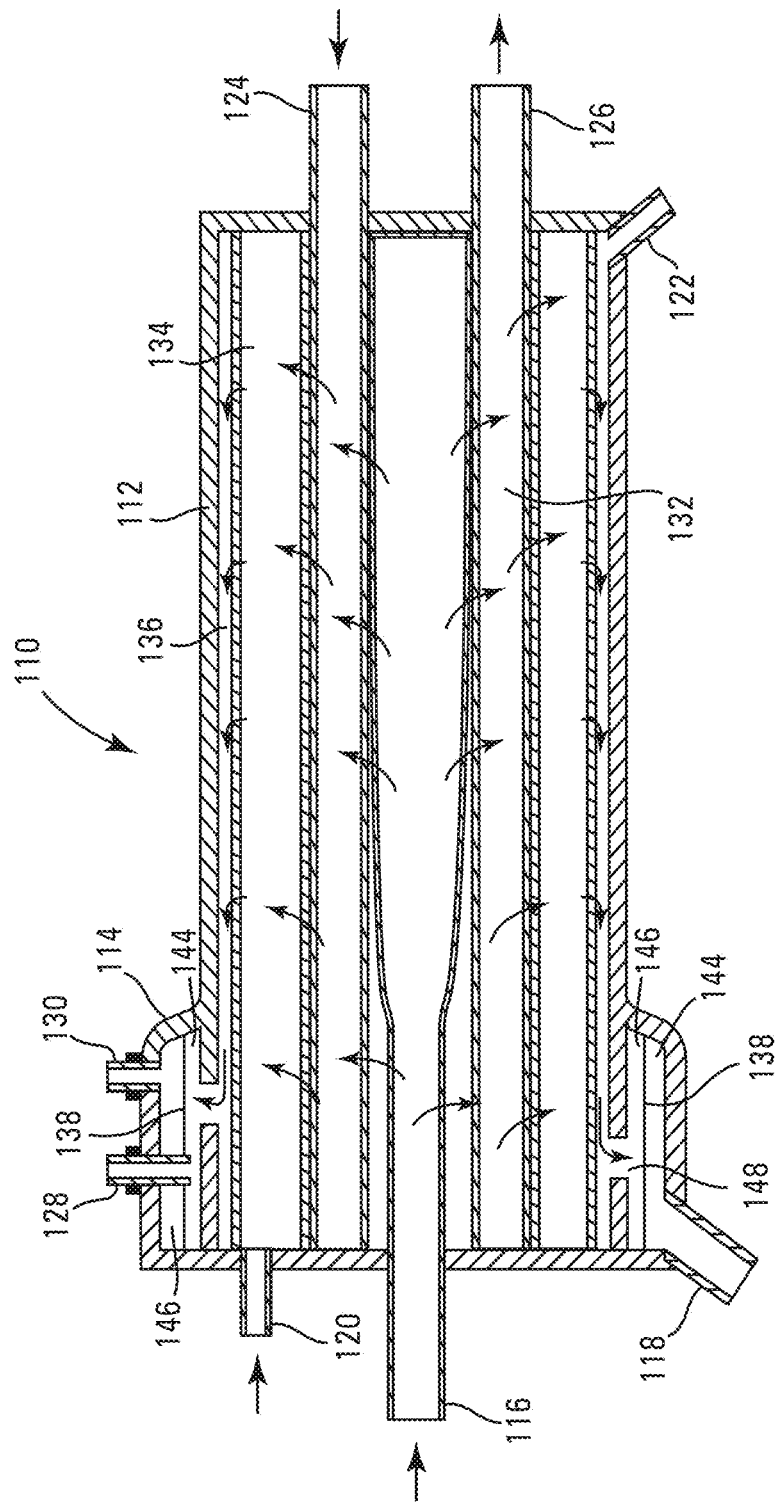
FIG. 6 is a schematic cross-sectional illustration of the blood processing apparatus of FIG. 5.

FIG. 6 is a cross-sectional view of the oxygenator 110, illustrating internal components of the oxygenator 110. The oxygenator 110 includes a heat exchanger 132 and a gas exchanger 134. In some embodiments, the heat exchanger 132 includes a number of hollow polymeric or metallic fibers through which a heating fluid such as water can flow. The blood may flow around and past the hollow fibers and thus be suitably heated. In some embodiments the gas exchanger 134 may include a number of hollow fibers through which a gas such as oxygen may flow. The blood may flow around and past the hollow fibers. Due to concentration gradients, oxygen may diffuse through the hollow fibers into the blood while carbon dioxide may diffuse into the hollow fibers and out of the blood.

As shown in FIG. 6, the gas exchanger is configured such that blood flows radially across the gas exchanger 134. In these embodiments, the oxygenator 110 includes an annular space 136 into which blood may flow as the blood exits the gas exchanger 134. According to various embodiments, the annular space 136 may be either open or it may be partially or completely filled with hollow fibers. As illustrated, the arterial filter housing 114 may extend over a portion of the annular space 136. According to other embodiments, the gas exchanger 134, the heat exchanger 132, or both may be configured such that blood is directed in a longitudinal flow path. In various exemplary embodiments where the gas exchanger 134 is configured such that blood flows in a longitudinal path, the annular space 136 is omitted. In these embodiments, the blood flows out of the gas exchanger 134 near an end and flows directly into the arterial filter housing 114. In some embodiments, the opening between the gas exchanger 134 and the arterial filter housing 114 is blocked or occluded at the radial location corresponding to the blood outlet 118 of the arterial filter housing 114, to minimize or prevent direct flow from the gas exchanger 134 into the blood outlet 118.

A filter 138 may be disposed within the arterial filter housing 114. In some instances, as illustrated, the filter 138 divides the space within the annular filter housing 114 into a first chamber 144 and a second chamber 146. An opening 148 that may extend circumferentially up to about 360 degrees provides fluid communication between the annular space 136 and the first chamber 144. While blood is in the first chamber 144, any air bubbles that are present within the blood may be vented through the first purge port 128. Blood may pass through the filter 138 and into the second chamber 146. Any bubbles remaining in the blood, or caused by passage through the filter 138, may be vented through the second purge port 130. Blood may then exit the oxygenator 110 through the blood outlet 118.

Figure 7:
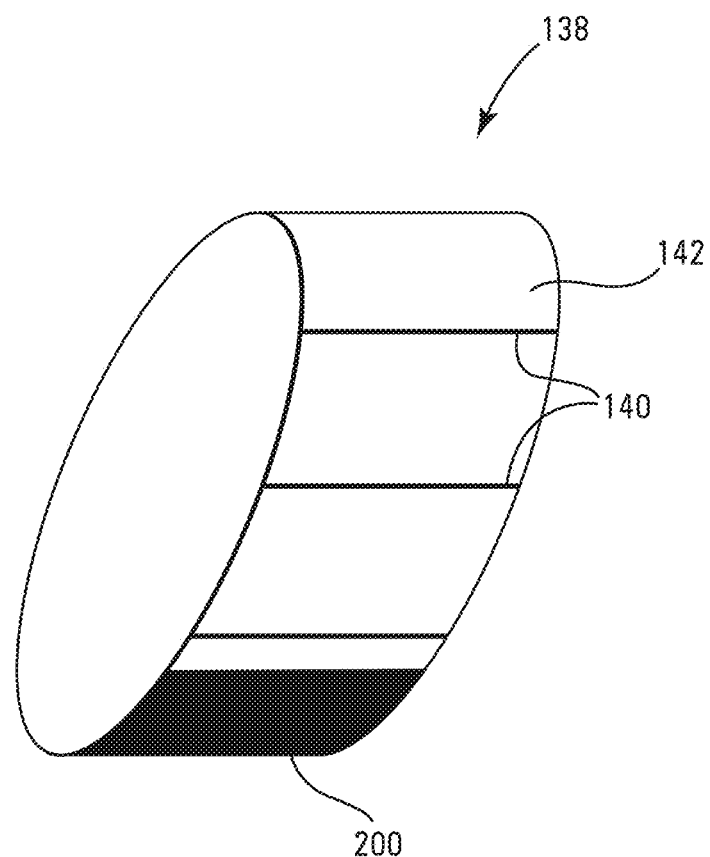
FIG. 7 is an illustrative view of a filter deployed within the blood processing apparatus of FIG. 5.

FIG. 7 is a view of the filter 138. In some embodiments, the filter 138 is a cylindrical filter that includes one or more reinforcements 140 and a cylindrical net or mesh 142. In some embodiments, the one or more reinforcements 140 may be molded into the cylindrical net or mesh 142. In some cases, the one or more reinforcements 140 may be adhesively secured to the cylindrical net or mesh 142. In some embodiments, the one or more reinforcements 140 may extend cylindrically about the filter 138. In some instances, the one or more reinforcements 140 may run across the filter 138.

In some embodiments, the net or mesh 142 may have a mesh size that is the range of about 20 to about 200 microns. In some cases, the net or mesh 142 may have a mesh size of about 120 microns. In some instances, the net or mesh 142 may have a mesh size of about 40 microns, and may be formed of a polymeric material such as polyester or polypropylene. In some cases, the net 142 may be coated with a biocompatible material.

In some embodiments, the net or mesh 142 may include a blocking region or plate 200 that is sized, shaped and positioned near the blood outlet 118 to limit preferential blood flow on the lower portion of the oxygenator 110. The blocking plate 200 may be formed of any suitable material. In some embodiments, the blocking plate 200 may be molded or otherwise formed within the net or mesh 142.

Figure 8:
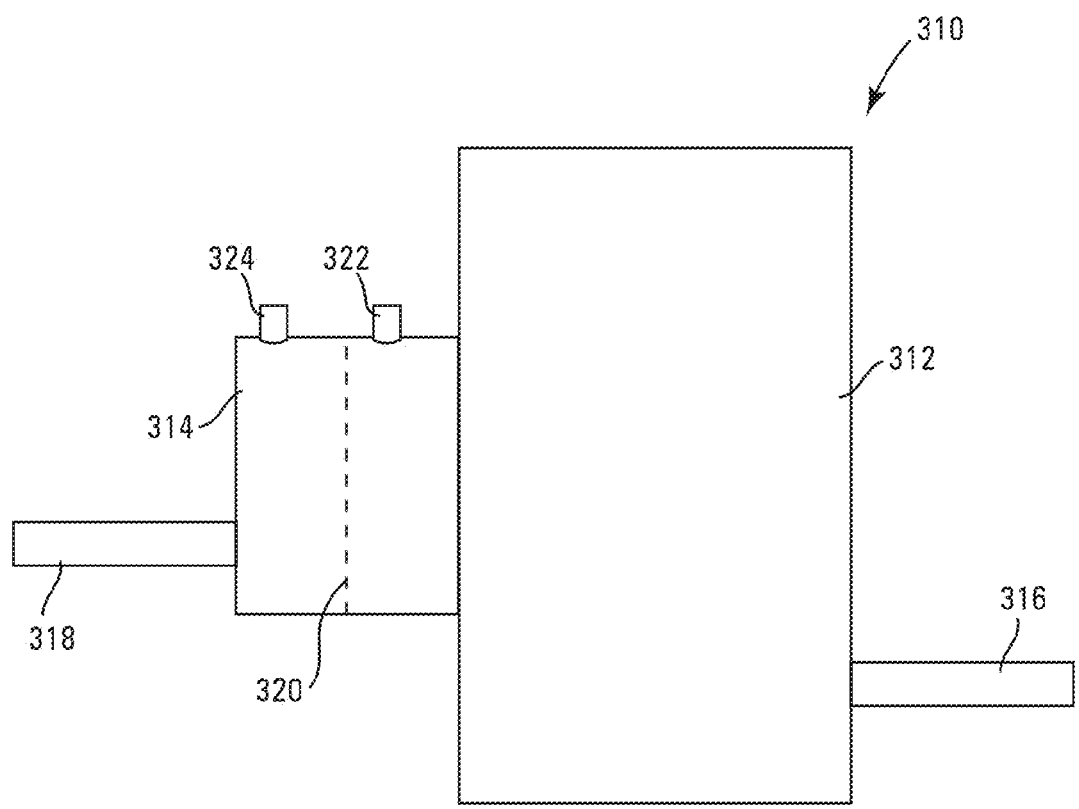
FIG. 8 is a schematic illustration of a blood processing apparatus including an integrated arterial filter in accordance with an embodiment of the invention.

FIG. 8 is a schematic illustration of a blood processing apparatus or oxygenator 310. While the internal components are not visible in this illustration, the oxygenator 310 may include one or more of a heat exchanger, a gas exchanger and an arterial filter. The oxygenator includes a device housing 312 and an arterial filter housing 314. In the illustrated embodiment, the arterial filter housing 314 is integrated into an end or side face of the device housing 312 and is configured such that blood exiting the device housing 312 enters the arterial filter housing 314. The device housing 312 includes a blood inlet 316 while the arterial filter housing 314 includes a blood outlet 318.

In some embodiments, as illustrated, the arterial filter housing 314 includes a net filter 320, a first purge port 322 and a second purge port 324. The first purge port 322 may be in fluid communication with an interior of the arterial filter housing 314 at a position upstream of the net filter 320 while the second purge port 324 may be in fluid communication with an interior of the arterial filter housing 314 at a position downstream of the net filter 320. As described in more detail above, this configuration allows an improvement and priming speed and efficacy, while also reducing the overall priming volume.

Figure 9:
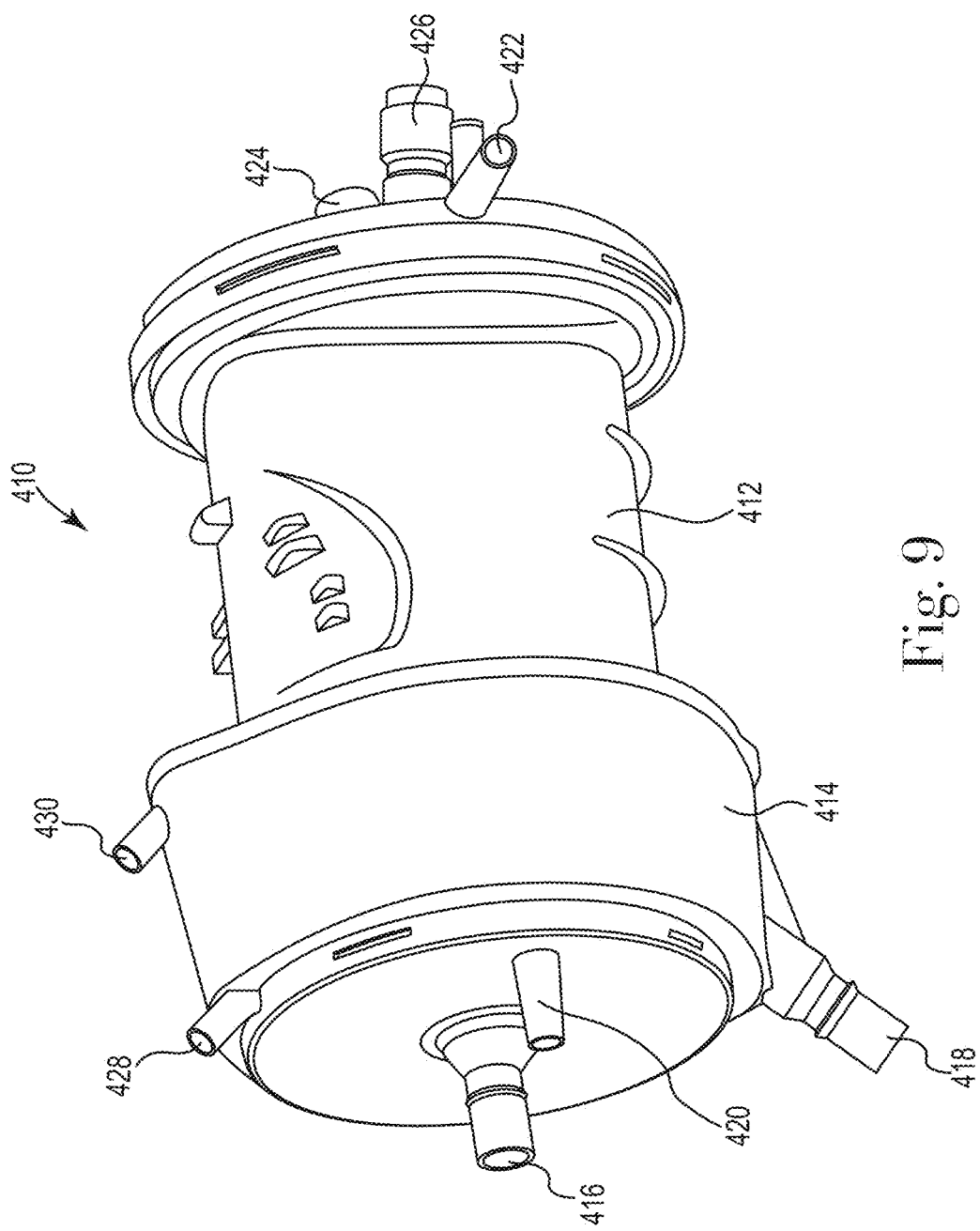
FIG. 9 is a perspective illustration of a blood processing apparatus including an integrated arterial filter in accordance with an embodiment of the invention.

FIG. 9 is a schematic illustration of a blood processing apparatus 410. While the internal components are not visible in this illustration, the blood processing apparatus 410 may include one or more of a heat exchanger, a gas exchanger and an arterial filter. According to some embodiments, each of the heat exchanger, gas exchanger and arterial filter are integrated into a single structure. The blood processing apparatus 410 includes an apparatus housing 412 and a filter housing 414. In some embodiments, the filter housing 414 may be integrally molded or otherwise structurally integrated with the apparatus housing 412. In some cases, the filter housing 414 may be separately formed and then secured or otherwise coupled to the apparatus housing 412. In some embodiments, as illustrated, the filter housing 414 may be considered as having a tapered or frustoconical shape.

In some embodiments, a blood inlet 416 extends through the filter housing 414 and into the apparatus housing 412. A blood outlet 418 exits the filter housing 414. As noted, in some embodiments the blood processing apparatus 410 includes a gas exchanger and thus may include a gas inlet 420 and a gas outlet 422. In some embodiments, the blood processing apparatus 410 includes a heat exchanger and thus may include a heating fluid inlet 424 and a heating fluid outlet 426. In some embodiments, the blood processing apparatus 410 may include a first purge port 428 and a second purge port 430. The positions of the inlets, outlets and purge ports are merely illustrative, as other arrangements and configurations are contemplated. The purge ports may include a valve or a threaded cap. The purge ports operate to permit gases (e.g., air bubbles) that exit the blood to be vented or aspirated and removed from the blood processing apparatus 410.

Figure 10:
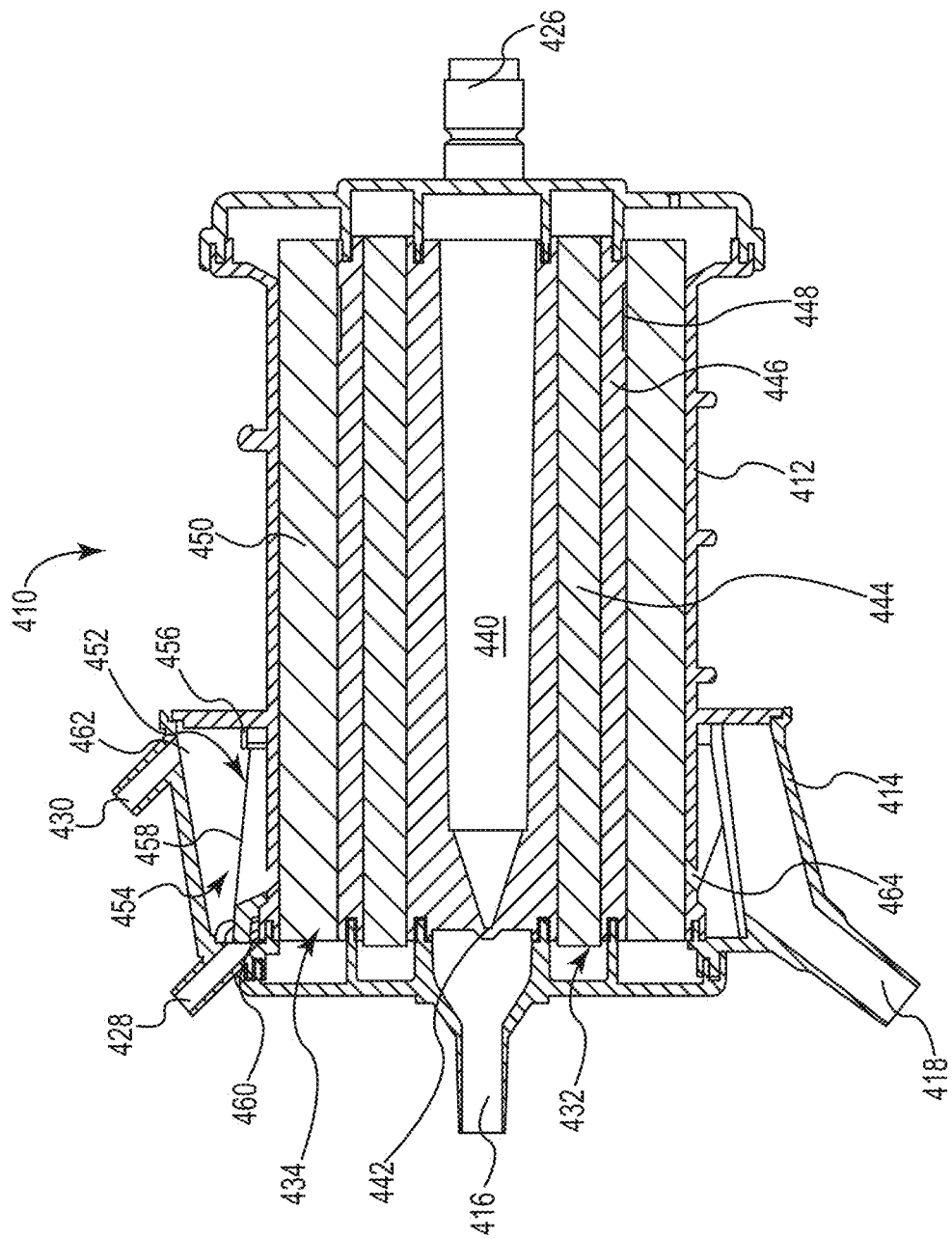
FIG. 10 is a cross-sectional view of the blood processing apparatus of FIG. 9.
Figure 11:
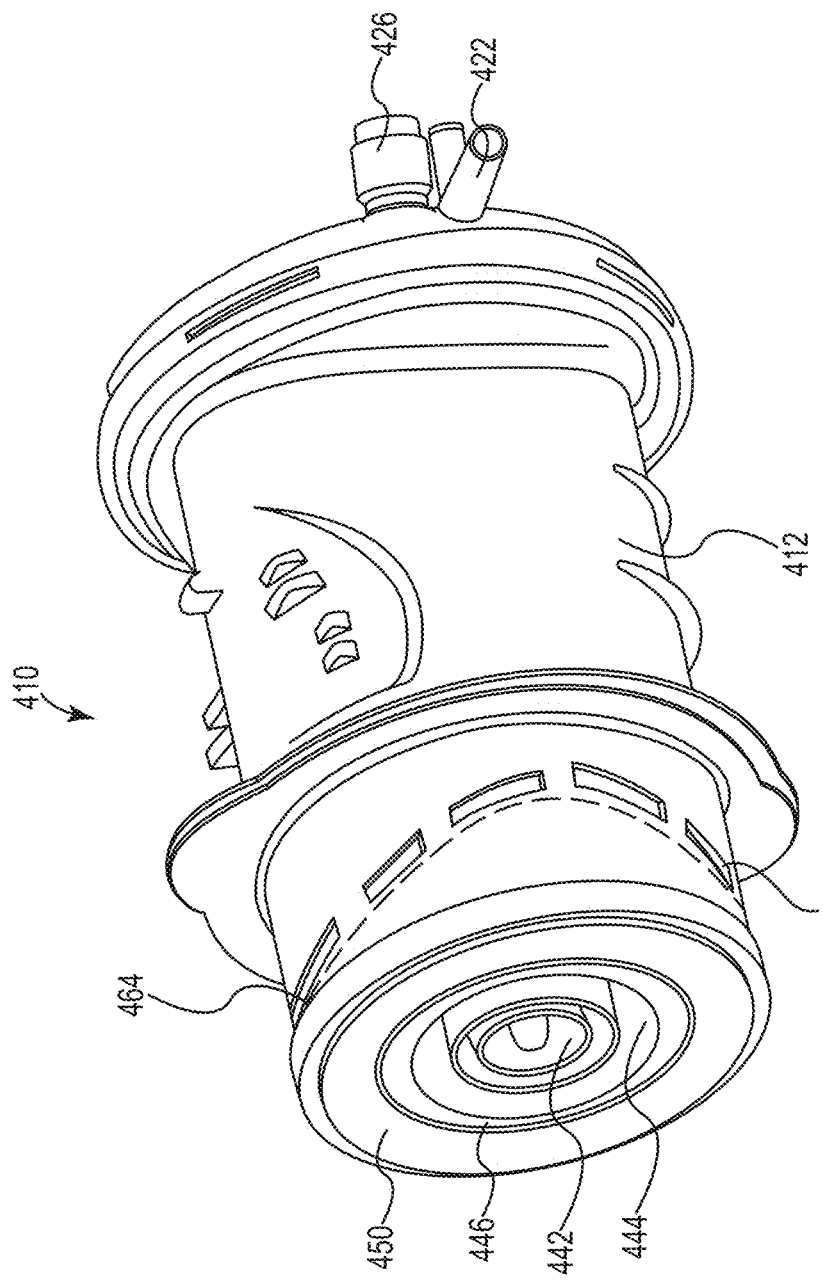
FIG. 11 is a perspective illustration of a portion of the blood processing apparatus of FIG. 9.
Figure 12:
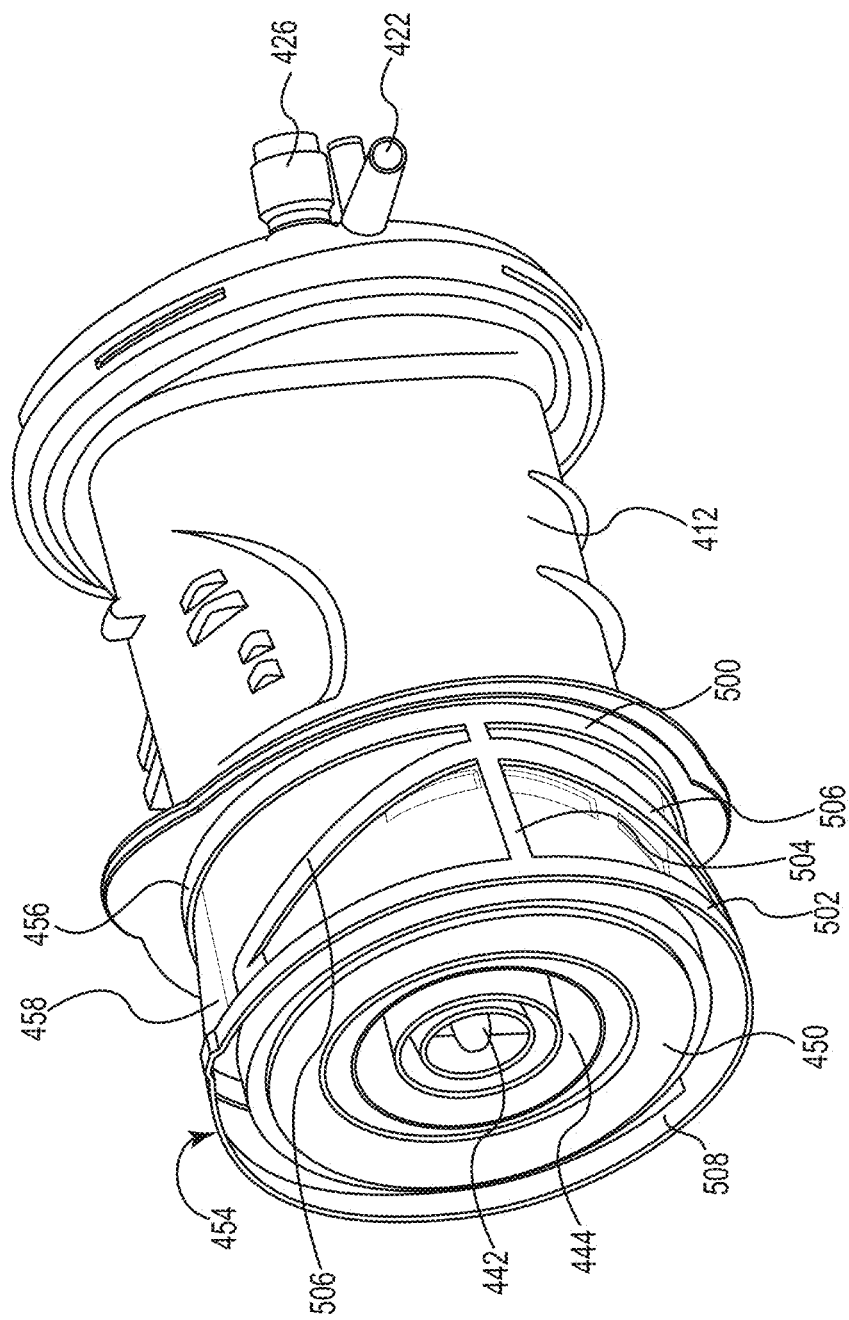
FIG. 12 is a perspective illustration of a portion of the blood processing apparatus of FIG. 9.

FIGS. 10, 11 and 12 further illustrate portions of the blood processing apparatus 410. FIG. 10 is a cross-sectional view of the blood processing apparatus 410, while FIGS. 11 and 12 are perspective views with some elements or features removed to illustrate underlying structure.

The blood processing apparatus 410 includes a heat exchanger 432 and a gas exchanger 434. In some embodiments, the heat exchanger 432 includes a heat exchanger core 440 including a blood diverter end 442 that is configured to divert blood exiting the blood inlet 416 past hollow fibers 444 through which a heating fluid (e.g., water) can flow. The blood may flow around and past the hollow fibers 444 and thus be suitably heated (or cooled). In some embodiments, the hollow fibers 444 may be polymeric. In some cases, metallic fibers may be used within the heat exchanger 432. According to other embodiments, the heat exchanger 432 includes a metal bellows or other structure comprising a substantial surface area (e.g., fins) for facilitating heat transfer with the blood. In some embodiments, the hollow fibers 444 are hollow polyurethane fibers having an outer diameter between about 0.2 and 1.0 millimeters or, more specifically, between about 0.25 and 0.5 millimeters. The hollow fibers may be woven into mats that can range from about 80 to about 200 millimeters in width. In some embodiments, the mats are in a criss-cross configuration.

In some embodiments, a cylindrical shell 446 may be disposed between the heat exchanger 432 and the gas exchanger 434. In some embodiments, the cylindrical shell 446 may be considered as delineating or defining a boundary between the heat exchanger 432 and the gas exchanger 434. In some embodiments, the cylindrical shell 446 prevents blood from migrating between the heat exchanger 432 and the gas exchanger 434 other than in desired locations. In order to permit blood exiting the heat exchanger 432 to enter the gas exchanger 434, in some embodiments the cylindrical shell 432 includes one or more shell apertures 448.

In the illustrated embodiment, the one or more shell apertures 448 are disposed near an end that is opposite that of the blood inlet 416. As a result, blood entering the heat exchanger 432 from the blood inlet 416 passes through at least a substantial portion of the heat exchanger 432 before the blood can exit the heat exchanger 432 through the one or more shell apertures 448 and into the gas exchanger 434.

In some embodiments the gas exchanger 434 may include a number of microporous hollow fibers 450 through which a gas such as oxygen may flow. The blood may flow around and past the hollow fibers 450. Due to concentration gradients, oxygen may diffuse through the microporous hollow fibers 450 into the blood while carbon dioxide may diffuse into the hollow fibers and out of the blood. In some embodiments, the hollow fibers 450 are made of polypropylene and have an outer diameter of about 0.38 millimeters. According to other embodiments, the microporous hollow fibers have a diameter of between about 0.2 and 1.0 millimeters or, more specifically, between about 0.25 and 0.5 millimeters. The hollow fibers 450 may be woven into mats that can range from about 80 to about 200 millimeters in width. In some embodiments, the mats are in a criss-cross configuration.

In some embodiments, as illustrated, the filter housing 414 defines a filter volume 452 between the filter housing 414 and the apparatus housing 412. A filter assembly 454, including a filter frame 456 and a filter net 458, divides the filter volume 452 into a first chamber 460 that is defined at least in part between the filter assembly 454 and the apparatus housing 412 and a second chamber 462 that is defined at least in part between the filter assembly 454 and the filter housing 414.

The filter frame 456 may be formed of any desired material such as a polymer. In some embodiments, the filter net 458 is a polyester net or a polypropylene net. In some embodiments, at least portions of the filter assembly 454 may be coated with a biocompatible material. In some embodiments, the first purge port 428 is in fluid communication with the first chamber 460 and the second purge port 430 is in fluid communication with the second chamber 462.

In some embodiments, blood passing through the gas exchanger 434 passes through one or more openings 464 into the first chamber 460 of the filter volume 452. At least some of the air bubbles, if any, within the blood may be purged through the first purge port 428. Blood may then pass through the filter net 458 into the second chamber 462 of the filter volume 452. Any air bubbles still within the blood may be purged through the second purge port 430 before the blood exits the blood processing unit 410 through the blood outlet 418.

The one or more openings 464 are best seen in FIG. 11. In some embodiments, as illustrated, the one or more openings 464 are disposed along an arcuate path. While in FIG. 11, the arcuate path is shown as concave relative to the end of the blood processing apparatus 410 at which the blood inlet 416 is located, in some embodiments the openings 464 may instead curve in a convex relation to the end of the blood processing apparatus 410. In some embodiments, the arcuate path may instead take a sinusoidal shape. The one or more openings 464 are sized and positioned to permit a desired volume of blood flow through the blood processing apparatus 410.

The filter assembly 454 is best seen in FIG. 12. In some embodiments, the filter frame 456 includes a first annular frame ring 500 having a first diameter and a second annular frame ring 502 having a second diameter that is greater than the first diameter. In some embodiments, as can be seen for example in FIG. 10, the filter housing 414 and the filter assembly 454 may both be tapered, but may taper in opposite directions. In some embodiments, tapering the filter assembly 454 can slow blood flow through the filter net 458 and can provide advantages in removing air bubbles from the blood. In some embodiments, an opposite taper in the filter housing 414 may further aid in bubble removal.

As shown in FIG. 12, the filter frame 456 includes one or more bridge elements 504 that extend between the first annular frame ring 500 and the second annular frame ring 502. The filter frame 456 also includes one or more arcuate ribs 506. By comparing FIGS. 11 and 12, it can be seen that the one or more arcuate ribs 506 are configured to align with the one or more openings disposed within the apparatus housing 412 along the arcuate path 464. As a result, and as will be described with respect to FIGS. 13 and 14, this alignment can deflect or otherwise impact (e.g., reduce) blood flow velocity through the filter volume 452. In some embodiments, if the path 464 is formed in a different shape than that illustrated, the one or more ribs 506 may be similarly shaped. In some embodiments, the filter frame 456 also includes a plate portion 508 that is arranged near the blood outlet 418 to limit preferential flow in the area near the blood outlet 418.

Figure 13:
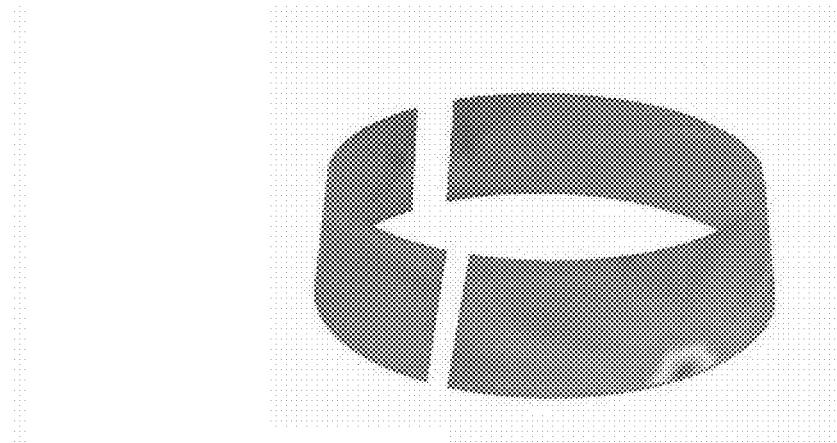
FIGS. 13 and 14 are schematic illustrations of blood flow showing how blood flow velocity is reduced in the blood processing apparatus of FIG. 9.
Figure 14:
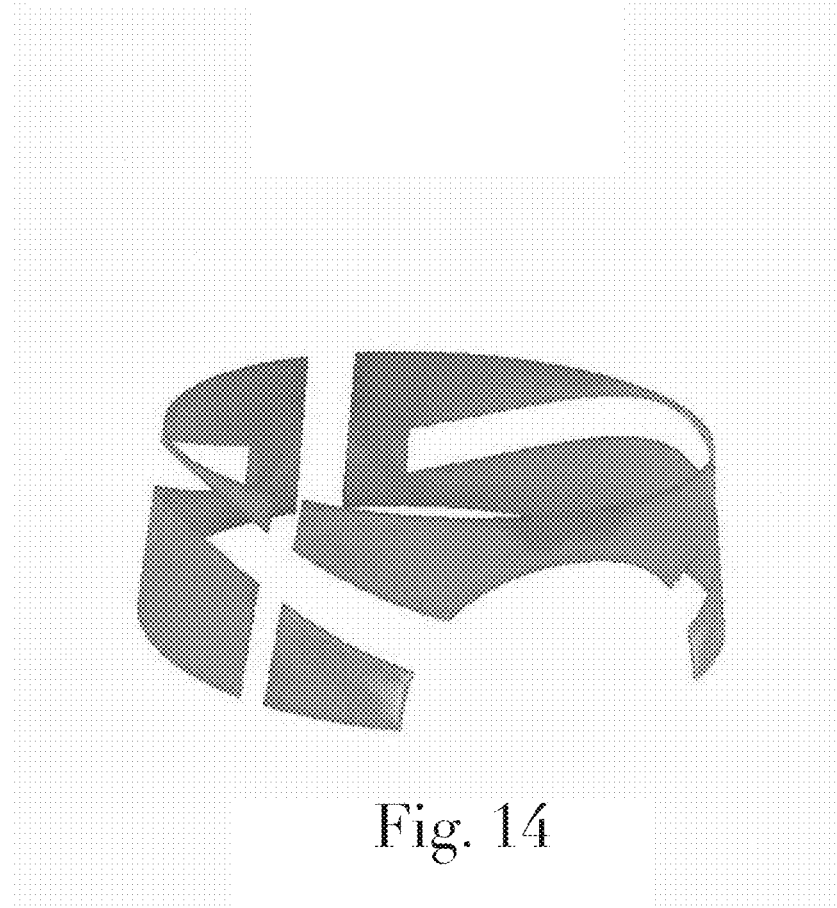

In some embodiments, the filter frame 456 is configured to regulate blood flow velocity through the filter assembly 454. FIG. 13 is a graphical representation of blood flow velocity through a filter lacking the filter frame 456 while FIG. 14 provides a graphical representation of blood flow velocity through the filter assembly 452. In both cases, the volumetric blood flow is quite similar, ranging from about 1.61 to about 1.63 liters per minute. These computerized modeling results reveal that the filter frame 456 reduces the maximum blood flow velocity through the filter by as much as 65 percent, without negatively impacting the volumetric blood flow.

Figure 15:
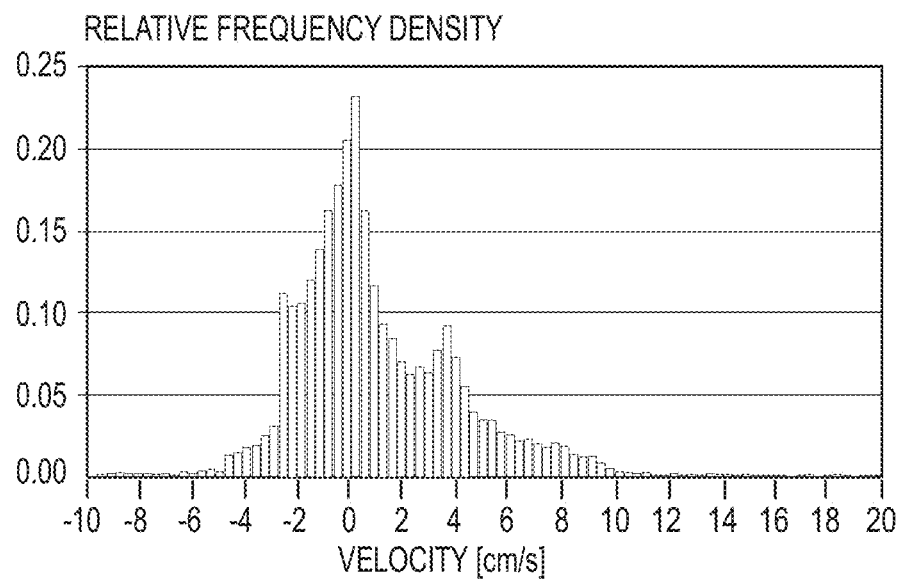
FIGS. 15 and 16 are graphical representations illustrating how backflow is reduced in the blood processing apparatus of FIG. 9.
Figure 16:
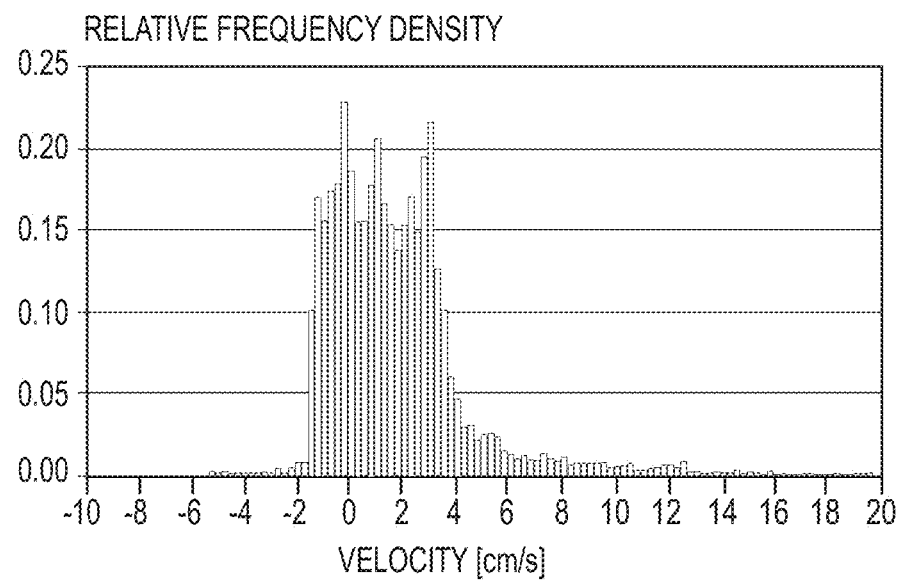

In some embodiments, backflow, or blood flowing backwards through the filter assembly can be problematic. FIGS. 15 and 16 are relative frequency density graphs, which show that backflow is reduced using the filter frame assembly 454. In these graphs, the relative amount of backflow can be seen by comparing the relative frequency of negative velocities with the relative frequency of positive velocities. Negative velocities represent blood flowing backwards through the filter net 458 while positive velocities represent blood flowing forwards, or in a desired direction, through the filter net 458.

In FIG. 15, which represents blood flow without the inventive filter frame assembly 454 and which corresponds to the velocity profile shown in FIG. 13, the total amount of backflow is about 51 percent of total blood flow. In FIG. 16, which represents blood flow with the inventive filter frame assembly 454 and which corresponds to the velocity profile shown in FIG. 14, the total amount of backflow is only about 16 percent.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A blood processing apparatus comprising:
an apparatus housing having a blood inlet and a blood outlet, the blood inlet extending into an interior of the apparatus housing;
a heat exchanger disposed about the blood inlet and in fluid communication therewith;
a gas exchanger disposed about the heat exchanger and in fluid communication therewith;
a filter housing coupled about the apparatus housing and defining a filter volume between the apparatus housing and the filter housing, the filter volume in fluid communication with the gas exchanger via one or more openings formed within the apparatus housing such that blood exiting the gas exchanger can pass into the filter volume; and a filter frame disposed within the filter housing, the filter frame having one or more ribs and a filter net disposed on the filter frame, the one or more ribs aligned with at least a portion of the one or more openings so as to reduce blood velocity through at least a portion of the filter net;

wherein the filter frame has a first annular frame ring having a first diameter and a second annular frame ring having a second diameter greater than the first diameter.

2. The blood processing apparatus of claim 1, wherein the one or more openings comprise a plurality of openings arranged along an arcuate path, and the one or more ribs comprise arcuate ribs aligned with the arcuate path.

3. The blood processing apparatus of claim 1, wherein the one or more ribs are disposed between the first annular frame ring and the second annular frame ring.

4. The blood processing apparatus of claim 1, wherein the filter frame includes a plate portion arranged near the blood outlet to limit preferential blood flow through the filter assembly near the blood outlet.

5. The blood processing apparatus of claim 1, wherein the filter assembly divides the filter volume into a first chamber between the filter assembly and the apparatus housing and a second chamber between the filter assembly and the filter housing.

6. The blood processing apparatus of claim 5, further comprising a first purge port in fluid communication with the first chamber and a second purge port in fluid communication with the second chamber.

7. The blood processing apparatus of claim 6, wherein the filter housing has a frustoconical configuration having a smaller diameter at one end and a larger diameter at an opposing end, and the second purge port is located near the larger diameter end of the filter housing.

8. The blood processing apparatus of claim 7, wherein the first purge port is located near the smaller diameter end of the filter housing.

9. The blood processing apparatus of claim 6, wherein bubbles within the blood can exit through the first purge port and/or the second purge port.

10. The blood processing apparatus of claim 1, wherein the gas exchanger is configured to permit gas to flow therethrough in order to add oxygen and remove carbon dioxide from the blood passing through the gas exchanger.

11. The blood processing apparatus of claim 1, wherein the filter assembly includes a biocompatible coating on the filter net.

12. The blood processing apparatus of claim 1, wherein the filter net comprises a polyester filter net or a polypropylene filter net.

* * * * *